United States Patent [19]

Maedgen, Jr.

[11] Patent Number: 4,646,683
[45] Date of Patent: Mar. 3, 1987

[54] METHOD AND APPARATUS FOR PRODUCING PARASITIC MITES

[75] Inventor: Malcolm A. Maedgen, Jr., Mathis, Tex.

[73] Assignee: Biofac, Inc., Mathis, Tex.

[21] Appl. No.: 786,670

[22] Filed: Oct. 11, 1985

[51] Int. Cl.[4] .............................................. A01K 67/00
[52] U.S. Cl. ........................................... 119/1; 119/15
[58] Field of Search ..................................... 119/1, 15

[56] References Cited

U.S. PATENT DOCUMENTS

| | | | |
|---|---|---|---|
| 3,941,089 | 3/1976 | Andreev et al. | 119/1 |
| 4,370,946 | 2/1983 | Voegele et al. | 119/1 |
| 4,411,220 | 10/1983 | Voegele et al. | 119/1 |
| 4,418,647 | 12/1983 | Hoffman | 119/1 |

Primary Examiner—Hugh R. Chamblee
Attorney, Agent, or Firm—Darryl M. Springs

[57] ABSTRACT

In one exemplar embodiment, method and apparatus are disclosed for producing parasitic mites in quantities sufficient for commercial use as a biological control agent for selected insect pests. A parent stock of the parasitic mites is produced of which the greatest proportion are gravid female mites. A quantity of selected insect hosts is prepared for parasitization by the parasitic mites. Then the selected insect hosts are introduced into close proximity to the parent stock of parasitic mites and separated therefrom by a screen for permitting host-seeking parasitic mite offspring to find the insect hosts. The insect hosts are then exposed to the parent stock of parasitic mites for a predetermined time period for parasitizing the insect hosts by the host-seeking parasitic mite offspring. The parasitized insect hosts are separated from the parent stock of parasitic mites and then incubated for a predetermined time period for producing a stock of adult parasitic mites of which the greatest proportion are gravid female mites that will produce host-seeking parasitic mite offspring for use as a biological control agent.

32 Claims, 13 Drawing Figures

METHOD AND APPARATUS FOR PRODUCING PARASITIC MITES

BACKGROUND OF THE INVENTION

This invention generally relates to a method and apparatus for producing parasitic mites in quantities sufficient for commercial use as a biological control agent for selected insect pests, and more particularly relates to a method and apparatus for producing commercial quantities of the straw itch mites, *Pyemotes tritici*, that can be useful as biological control agents against selected insect pests.

Biological control of pests is a program in which certain selected beneficial organisms are manipulated to reduce a pest population below its economic injury threshold. One effective manipulative technique that has been successfully utilized to enhance biological control is the augmentation of natural enemies of selected pests. To achieve a successful program, mass releases of the beneficial organisms (predators or parasites) must be effected in order to be effective in a field situation. It has been suggested from time to time that pyemotid mites can successfully be used as control agents for stored-product pests, and certain laboratory experimentation has provided valuable information regarding the effectiveness of the straw itch mite, *Pyemotes tritici* (hereinafter referred to as the "parasitic mite"), on selected stored-product pests such as the angoumois grain moth, cigarette beetle, Indian meal moth, merchant grain beetle, red flour beetle, almond moth, sawtooth weevil, rusty grain beetle, lesser grain borer, rice weevil and many others. In addition, it has also been found that the parasitic mite can be an effective parasite in controlling and destroying fire ant colonies. However, rearing parasitic mites in the laboratory does not easily equate to methods and apparatus for producing such parasitic mites in commercial quantities for mass-release in the field.

BRIEF SUMMARY OF THE INVENTION

In accordance with this invention, a method is disclosed of producing parasitic mites in quantities sufficient for commercial use as a biological control agent for selected insect pests. The method comprises the steps of producing a parent stock of the parasitic mites of which the greatest proportion are gravid female mites, preparing a quantity of selected insect hosts for parasitization by the parasitic mites, introducing the selected insect hosts into close proximity to the parent stock of parasitic mites for permitting host-seeking parasitic mite offspring to find the insect hosts, exposing the insect hosts to the parent stock of parasitic mites for a predetermined time period for parasitizing the insect hosts by the host-seeking parasitic mite offspring, separating the parasitized insect hosts from the parent stock of parasitic mites, and incubating the parasitized insect hosts for a predetermined time period for producing a stock of adult parasitic mites of which the greatest proportion are gravid female mites that will produce host-seeking parasitic mite offspring for use as a biological control agent. It has been found that the Angoumois grain moth, *Sitotroga cerealla*, is especially well suited for use as the host, since it is readily available and may be used in its adult, larval or pupal stages. If it is used in its adult stage, the preparing step includes the step of descaling the adult moths to increase their vulnerability to the host-seeking parasitic mites. If the larval or pupal stages of the Angoumois grain moth are used, the preparing step includes the step of rearing the moth larva or pupa in a selected seed carrier.

In addition, the introducing step includes the step of screening the quantity of selected insect hosts from the parent stock of parasitic mites for preventing mixture of the insect hosts with the parent stock of parasitic mites but allowing the host-seeking parasitic mite offspring access to the insect hosts. For adult moths it has been found that the exposure time of the adult moths to the parasitic mites is optimally approximately 24 hours, while such exposure time using the moth larvae or pupae is approximately 72 hours. In addition, the method can further include the step of packaging the incubated parasitic mites and parasitized hosts for shipment to use as a biological control agent, and can further include the step of sealing the incubated parasitic mites and parasitized hosts in gas-permeable containers for permitting entry of air but preventing escape of the parasitic mites.

According to another principle of the invention, apparatus is disclosed for producing parasitic mites in quantities sufficient for commercial use as a biological control agent for selected insect pests, comprising a container carrying a parent stock of the parasitic mites of which the greatest proportion are gravid female mites, a quantity of selected insect hosts, separating means for introducing the selected insect hosts into the container in close proximity to the parent stock of parasitic mites and preventing mixture of the insect hosts with the parent stock of parasitic mites but permitting the host-seeking parasitic mite offspring access to the selected insect hosts, the insect hosts being exposed to the parent stock of parasitic mites for a predetermined time period for permitting parasitization of the insect hosts by the host-seeking parasitic mite offspring, an incubator for receiving and incubating said parasitized insect hosts for a predetermined time period for producing a stock of adult parasitic mites of which the greatest proportion are gravid female mites that will produce host-seeking parasitic mite offspring for use as a biological control agent. When the adult Angoumois grain moth is used as the host, the apparatus further includes a means for descaling the adult moths for increasing the vulnerability of the moths to the host-seeking parasitic mites. When the larval or pupal stage of the moths are used as the hosts, the quantity of selected hosts also includes a quantity of a preselected seed carrier for biologically supporting the moth larvae or pupae.

The separating means of the apparatus comprises a screen sized to cover the parent stock of parasitic mites in the container and support the quantity of selected insect hosts (and seed carrier, as the case may be) the screen material having a mesh size small enough to prevent mixture of the insect hosts with the parent stock of parasitic mites but which allows the host-seeking parasitic mite offspring access to the insect hosts. According to another principle of the invention, shipping means may be provided for packaging the incubated parasitic mites and parasitized hosts for shipment for use as a biological control agent. The shipping means comprises a shipping container for receiving the parasitic mites and parasitized hosts for commercial shipment, the container sealable to prevent escape of the parasitic mites but being constructed of a gas-permeable material that permits entry of air.

Accordingly, one primary advantage of the present invention is the disclosure of method and apparatus for producing parasitic mites in commercial quantities suitable for mass release as a biological control agent.

Another advantage of the present invention is the provision of method and apparatus for economically producing the parasitic mites in commercial quantities.

Yet another advantage of the present invention is the provision of method and apparatus for producing in commercial quantities parasitic mites that are useful in biological control of a wide variety of stored-product insect pests and other insects such as the imported fire ant.

Still another advantage of the present invention is the provision of method and apparatus for producing in commercial quantities a closely synchronized generation of parasitic mites that will have a rapid impact on the desired insect pest population.

BRIEF DESCRIPTION OF THE DRAWINGS

In order that the manner in which the above-recited advantages and features of the invention are achieved can be understood in detail, a more particular description of the invention will now be made by reference to specific embodiments thereof which are illustrated in the accompanying drawings, which drawings form a part of this specification.

In the drawings.

DETAILED DESCRIPTION OF THE INVENTION

As previously discussed, the use of parasitic mites, such as the straw itch mite, *Pyemotes tritici*, (hereinafter referred to as the "parasitic mites"), as biological control agents of stored-product insect pests has been suggested for some time and laboratory results have been promising. In addition it has been found that the parasitic mites are also effective to destroy imported fire ants. However, the real problem has been in translating laboratory test results into an effective biological control program in the field, where mass releases of the mites is necessary to establish an effective control. To better understand the method and apparatus that has been developed to rear and produce the parasitic mites in large quantities suitable for commercial use as a biological control agent, it will be helpful to understand the basic life cycle of the mites.

Figure 1A:
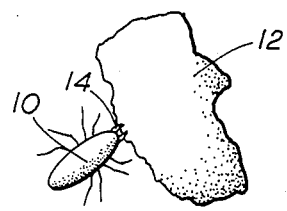
FIG. 1A is a pictorial drawing (greatly enlarged) of an adult parasitic mite feeding on a host.
Figure 1B:
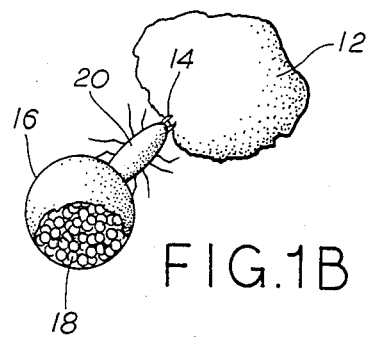
FIG. 1B is a pictorial drawing (greatly enlarged) of an adult gravid female parasitic mite feeding on a host.
Figure 1C:
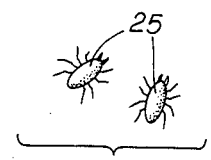
FIG. 1C is a pictorial drawing (greatly enlarged) of immature host-seeking parasitic mite offspring after emerging from the egg sac of a gravid female.

Referring now to FIG. 1A, a pictorial drawing, greatly enlarged, shows a parasitic mite 10 preying on an insect host 12 (only shown partially) by means of its piercing and sucking mouth parts 14. The parasitic mite 10 is able to inject a minute amount of a toxin into the host 12, immobilizing the host and allowing for uninterrupted feeding and parasite development. FIG. 1B is a pictorial drawing of a gravid female parasitic mite 20 that is feeding on a parasitized host 12 and attached thereto by its mouth parts 14. As the female mite 20 matures (4-7 days) it produces eggs 18 in an egg sac 16 (the female having been mated and fertilized by a male parasitic mite upon emergence). In 3-6 days the eggs 18 mature within the sac 16 and produce mature host-seeking parasitic mites 25 (see FIG. 1C) which emerge and being actively seeking hosts. The ratio of females to males is roughly 9 to 1 and the females are mated and fertilized by the male mites upon emergence from the egg sac as hereinabove described.

Figure 2:
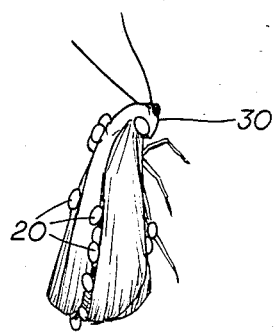
FIG. 2 is a pictorial drawing (greatly enlarged) showing an adult Angoumois grain moth parasitized by a plurality of gravid female parasitic mites.
Figure 3:
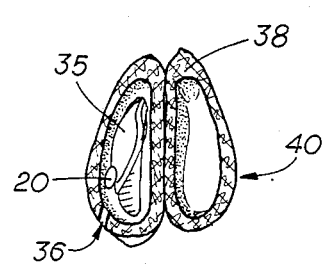
FIG. 3 is a pictorial drawing (greatly enlarged) of a wheat seed that has been split open to reveal a moth larva (pupa) therein that has been parasitized by at least one gravid female parasitic mite.

In FIG. 2, an adult Angoumous grain moth 30 is shown having been parasitized by numerous parasitic mites, of which the gravid female mites 20 are the most prominent. FIG. 3 is an enlarged pictorial representation of a wheat seed 38 split in half to reveal the host larval or pupal stage of the Angoumois grain moth 35 that has bored into the seed through entry passage 36. A gravid female parasitic mite 20 is shown preying on the host larva (or pupa) 35 with its enlarged egg sac. The combination of the gravid female parasitic mite 20, the host larva (or pupa) 35 and the seed in which they are carried (the "carrier") very be referred to in combination as the parasitic mite/host/carrier 40.

Figure 4:
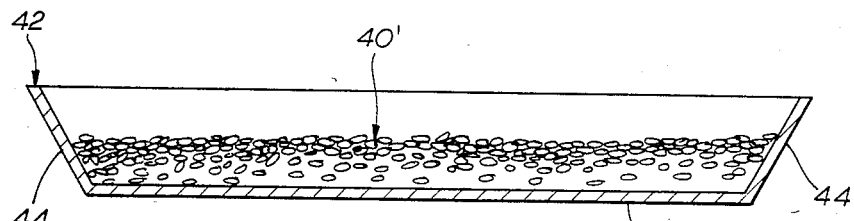
FIG. 4 is a vertical cross-sectional view of a container carrying the parent stock of the parasitic mites in a seed product carrier.
Figure 4A:
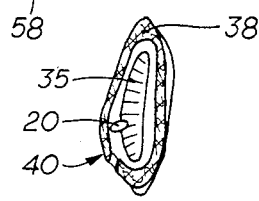
FIG. 4A is an enlarged view of one seed, partially cut-away, for showing the parasitized host larva or pupa.

FIG. 4 shows a tray 42 constructed of any suitable material, such as a rigid plastic, and having side walls 44 and a bottom 46 for receiving and carrying a quantity of parasitic mite/host/carrier 40 that comprises a quantity of a parent stock 40' of the parasitic mites of which the greatest proportion are gravid female mites. A cut-away enlarged view of an individual combination parasitic mite/host/carrier seed 40 is also shown in FIG. 4A. The parasitic mites present in the parent stock 40' are predominantly gravid female mites 20 from which the eggs will hatch and produce host-seeking offspring mites for 7-14 days depending on the continued availability of a parasitized host to sustain the female and temperature and humidity conditions.

Figure 5:
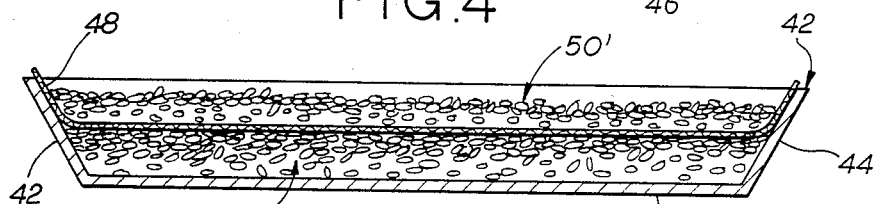
FIG. 5 is a vertical cross-sectional view of a container carrying the parent stock of parasitic mites in the same seed product carrier as shown in FIG. 4, but showing the parent stock of parasitic mites covered by a screen material overlaid with a quantity of selected insect hosts (larval or pupal stage) carried in a quantity of seed products.
Figure 5A:
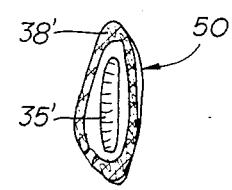
FIG. 5A is an enlarged view of one seed product used in the tray arrangement of FIG. 5, partially cut-away, showing the host (larval or Pupal stage) carried by the seed product.

In FIG. 5, the tray or container 42 is as shown in FIG. 4 carrying the parent stock of parasitic mites 40', and is covered with a screening material 48 and then a quantity of prepared select insect hosts 50' are placed in the container above the screening material. An individual seed carrier 38' is shown in FIG. 5A with an unparasitized host 35' (larval or pupal stage) is shown, and will sometimes be referred to as a host/carrier 50. The screen material 48 may be constructed of any suitable screening material, the mesh size of which is small enough to prevent the seeds 38' of the selected insect hosts 50' from falling through the screen 48 and mixing with the seeds 38 of the parent stock of parasitic mites 40', but are sufficiently large enough to permit host-seeking parasitic mites from the parent stock 49' access to the quantity of selected insect hosts 50'. If the selected hosts are the larval (pupal) stages of the insect, the hosts must be "prepared" by rearing the larvae (or pupae) for a desired time period in a "carrier", namely the seed 38', to properly develop the host larvae (or pupae) 35' for parasitization.

The selected hosts/carriers 50' (larvae or pupae) are exposed to the host-seeking parasitic mites 25 hatching from the egg sacs of the gravid females 20 present in the parent stock of parasitic mites 40' for a period of approximately 72 hours. This exposure provides sufficient time for the host-seeking parasitic mite offspring to "find" the host larvae (or pupae) 35' for parasitization and continuing adult development.

After 72 hours, the quantity of parasitized selected insect hosts 50' are removed from the container 42 and either used as "parent stock" 40' in parasitizing new insect hosts or placed in an incubator for a predetermined time period as will be hereinafter further described.

Figure 6:
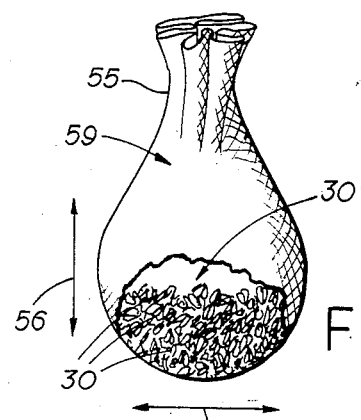
FIG. 6 is a side elevational view, partially cut-away, of one means for descaling adult Angoumois grain moths to be used as insect hosts.
Figure 7:
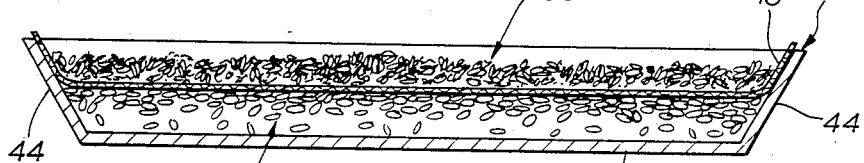
FIG. 7 is a vertical cross-sectional view of a container carrying the parent stock of parasitic mites in the same seed product carrier as shown in FIG. 4, but showing the parent stock of parasitic mites covered by a screen material overlaid with a quantity of descaled adult moths.
Figure 8:
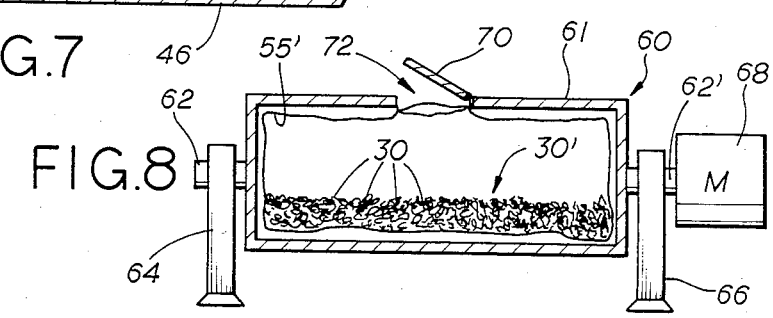
FIG. 8 is a vertical cross-sectional view of a second embodiment of apparatus for descaling adult Angoumois grain moths to be used as insect hosts.

Referring to FIGS. 6, 7 and 8, if the quantity of insect hosts is selected to be the adult stage of the Angoumois grain moth, it is preferable to "prepare" the adult moths 30 by first "descaling" the moths to make them more vulnerable to the host-seeking parasitic mites. This descaling step may be accomplished by hand by vigorously shaking (directions 56–58) the moths 30 in a sack 55 of a smooth material that will effectively remove the scales from the moth bodies but will not injure the moths. In addition, the mesh 59 of the bag should be small enough to retain the moths but large enough to permit the escape of the scales.

Another simple embodiment of a descaling apparatus 60 is shown in FIG. 8. A drum 61 has a pair of shafts 62—62' axially projecting therefrom and journaled for rotation in a pair of brackets 64 and 66. A motor 68 is coupled to shaft 62' for rotating the drum 61. The interior of drum 61 is lined with a suitable material 55' to accomplish the descaling. A quantity of the selected adult moths 30' are placed in the interior of drum 61 and cover material 55' through an opening 72. The access door 70 is closed and secured, and the motor 68 is switched on to rotate the drum and descale the moths. Under most circumstances, the descaling time is approximately 30 seconds.

It is also beneficial to cool the body temperature of the descaled moths 30 down to about 40° F. for a period of time, until the descaled moths' metabolism slows and immobilizes them. This immobilization is due to the lowered body temperature and makes them easier to handle and increases the rate of parasitism by the mites.

Figure 7A:
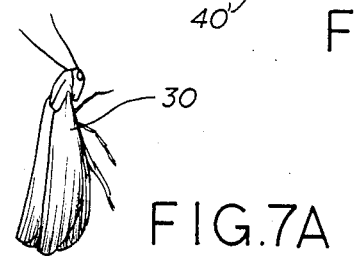
FIG. 7A is an enlarged view of one of the adult insect moths used as hosts.

FIG. 7 shows the tray 42, as shown in FIG. 4, carrying the parent stock of parasitic mites 40', but is covered with a screening material 48, just as above described for FIG. 5, and carrying and supporting a quantity of descaled adult moths 30' (see FIG. 7A). The screening material 48 may be constructed of any suitable screening material, the mesh size of which is small enough to prevent the adult moths 30 from passing through the screen 48 and mixing with the parent stock 40' of parasitic mites, but is sufficiently large enough to permit host-seeking parasitic mites from the parent stock 40' access to the quantity of selected adult hosts 30. Since it is easier for the parasitic mites to find and prey on the adult descaled moths, the exposure time to achieve parasitization of the quantity of selected adult moths is only about 24 hours. Then the quantity of parasitized adult moths 30' is removed from container 42 and either placed in an incubator for further maturation or used as "new" parent stock 40' to parasitize another quantity of selected hosts 30', 40' or 50'.

The success of the process of parasitizing selected hosts and producing parasitic mites in commercial quantities is largely dependent on temperature and the relative humidity. The optimum temperature for maximizing production has been found to be 80° F. with a relative humidity of 80%. However, production will continue to occur in the temperature range of 65° F. to 95° F. and at relative humidities as low as 30% or as high as 100%. Below 65° F. production slows appreciably, and at temperatures above 95° F., especially if the relative humidity is low, say below 50%, the mortality rate increases and production drops.

The optimum ratio of parent stock (parasitic mite/host/carrier) 40' to the selected insect host 59' to be parasitized is approximately 3:1 with some variation between the time the parasitized hosts begin producing parasites and the time the parasitized hosts stop producing parasites, which is related to the amount of host biomass available to the parasitic mites. The ratio would be smaller for parasitizing adult moths 30' since their biomass is greater and they are easier to parasitize than larvae (or pupae) inside of seeds.

Incubation time is a function of a number of variable factors such as parasite/host ratios, environmental conditions, suitability of the host, and others. Under optimum conditions, including a temperature of 80° F. and a relative humidity of 80%, the incubation time is 72 hours. The incubation time permits the gravid female parasitic mites time to mature and maximize the number of host-seeking parasitic mites that will be produced.

There are many different kinds of grain seeds suitable for propogation of the selected insect host in either the larval or pupal stage. However, wheat is ideal, especially for the larval or pupal stage of the Angoumois grain moth, since it is a long narrow seed that is the same shape of the host and slightly larger, and provides an ideal environment for the internal feeding and development of the host. The average size of a wheat seed carrier 38 (38') is 3/32×¼ inches, while the Angoumois grain moth host larva and pupa average in size of about 1/16×3/16 inches. The average size of the adult Angoumois grain moth host is about 3/32×¼ inches.

The parasitic mites, *Pyemotes tritici,* under optimum conditions of food (host), temperature, humidity, etc. may live as long as 3 weeks in the productive stage, and as long as 7–8 weeks if stored at 60° F. on the 5th day of post-parasitism. However, without a host, the mites will normally live only 3–5 days.

After incubation, the parasitized hosts (and seed carriers in the case of host larvae or pupae) may be packaged in suitable containers for commercial shipment. The containers may be of any suitable material, at least a portion of which is gas-permeable to permit entry of air, but which is sealable to prevent the escape of the parasitic mites. Of course suitable precautions must be taken to protect against bites from the mites by humans handling and opening the shipping containers.

One example of a suitable container for shipping the parasitic mites is an open container of rigid plastic that is closable by a press-to-fit paperboard lid. The plastic container provides rigidity and strength, and the paperboard lid allows for gas-permeability and entry of air therethrough. The lid may be sealed to prevent escape of the parasitic mites by a suitable adhesive or glue.

From the foregoing, it can be seen that the novel method and apparatus provides a technique of producing a closely synchronized generation of parasitic mites. Since the selected hosts are separated from the parent stock and the exposure time to the host-seeking offspring is carefully controlled, the parasitized hosts will carry a generally uniform or "synchronized" generation of parasitic mites, all generally of the same stage development. This "synchronization" minimizes risks to the developing parasites due to changes in environmental conditions and predation from other insect pests.

Numerous variations and modifications may be made in the methods and structures herein described without departing from the present invention. Accordingly, it should be understood that the form of the invention herein described in the figures of the accompanying drawings are illustrative only and are not intended to limit the scope of the invention.

I claim:

1. A method of producing parasitic mites in quantities sufficient for commercial use as a biological control agent for selected insect pests, comprising the steps of
   producing a parent stock of the parasitic mites of which the greatest proportion are gravid female mites,
   preparing a quantity of selected insect hosts for parasitization by the parasitic mites,
   introducing said selected insect hosts into close proximity to said parent stock of parasitic mites, for permitting host-seeking parasitic mite offspring to find said insect hosts,
   exposing said insect hosts to said parent stock of parasitic mites for a predetermined time period for parasitizing said insect hosts by said host-seeking parasitic mite offspring,
   separating said parasitized insect hosts from said parent stock of parasitic mites, and
   incubating said parasitized hosts for a predetermined time period for producing a stock of adult parasitic mites of which the greatest proportion are gravid female mites that will product host-seeking parasitic mite offspring for use as a biological control agent.

2. The method of claim 1, wherein the parasitic mite is the straw itch mite, *Pyemotes tritici.*

3. The method of claim 1, wherein said incubating step predetermined time period is approximately seventy-two hours.

4. The method of claim 1, wherein said insect hosts are the adult stage of the Angoumois grain moth, *Sitotroga cerealla.*

5. The method of claim 4, wherein said preparing step includes the step of descaling said adult Angoumois grain moths for increasing the vunerability of said moths to said host-seeking parasitic mites.

6. The method of claim 5, wherein said introducing step includes the step of screening said quantity of adult moths from said parent stock of parasitic mites for preventing mixture of said moths with said parent stock of parasitic mites but allowing said host-seeking parasitic mite offspring access to said moths.

7. The method of claim 5, wherein exposing step predetermined time period is approximately twenty-four hours for said adult moths.

8. The method of claim 1, wherein said insect hosts are the larva stage of the Angoumois grain moth, *Sitotroca cerealla.*

9. The method of claim 8, wherein said preparing step includes the step of rearing said moth larva in a preselected seed carrier.

10. The method of claim 9, wherein said introducing step includes screening said preselected quantity of moth larva and said seed carrier from said parent stock of parasitic mites for preventing mixture of said moth larva and said seed carrier with said parent stock of parasitic mites but allowing said host-seeking parasitic mite offspring access to said moth larva in said seed carrier.

11. The method of claim 9, wherein said exposing step predetermined time period is approximately seventy-two hours for said moth larvae.

12. The method of claim 1, wherein said insect hosts are the pupa stage of the Angoumois grain moth, *Sitotroga cerealla.*

13. The method of claim 12, wherein said preparing step includes the step of rearing said moth pupa in a preselected seed carrier.

14. The method of claim 13, wherein said introducing step includes screening said preselected quantity of moth pupae and said seed carrier from said parent stock of parasitic mites for preventing mixture of said moth pupae and said seed carrier with said parent stock of parasitic mites but allowing said host-seeking parasitic mite offspring access to said moth pupae in said seed carrier.

15. The method of claim 13, wherein said exposing step predetermined time period is approximately seventy-two hours for said moth pupae.

16. The method of claim 1, further including the step of packaging said incubated parasitic mites and parasitized hosts for shipment to use as a biological control agent.

17. The method of claim 16, wherein said packaging step includes sealing said incubated parasitic mites and parasitized hosts in an at least partially gas-permeable container for permitting entry of air but preventing escape of said parasitic mites.

18. Apparatus for producing parasitic mites in quantities sufficient for commercial use as a biological control agent for selected insect pests, comprising
   a container carrying parent stock of the parasitic mites of which the greatest proportion are gravid female mites,
   a quantity of selected insect hosts,
   separating means for introducing said selected insect hosts into said container in close proximity to said parent stock of parasitic mites for preventing mixture of said insect hosts with said parent stock of parasitic mites but permitting the host-seeking parasitic mite offspring access to said selected insect hosts, said insect hosts being exposed to said parent stock of parasitic mites for a predetermined time period for permitting parasitization of said insect hosts by said host-seeking parasitic mite offspring, and an incubator for receiving and incubating said parasitized insect hosts for a predetermined time period for producing a stock of adult parasitic mites of which the greatest proportion are gravid female mites that will produce host-seeking parasitic mite offspring for use as a biological control agent.

19. The apparatus of claim 18, wherein the parasitic mite is the straw itch mite, *Pyemotes tritici*.

20. The apparatus of claim 18, wherein said separating means comprises a screen sized to cover said parent stock of parasitic mites in said container and to support said quantity of selected insect hosts, said screen having a screen material of a mesh size small enough to prevent mixture of said quantity of insect hosts with said parent stock of parasitic mites but which allows said host-seeking parasitic mite offspring access to said insect hosts.

21. The apparatus of claim 18, wherein said incubation predetermined time period is approximately seventy-two hours.

22. The apparatus of claim 18, wherein said insect hosts are the adult stage of the Angoumois grain moth, *Sititroga cerealla*.

23. The apparatus of claim 22, further including means for descaling said adult Angoumois grain moths for increasing the vulnerability of said moths to said host-seeking parasitic mites.

24. The apparatus of claim 22, wherein said exposure predetermined time period is approximately twenty-four hours for said adult moths.

25. The apparatus of claim 18, wherein said insect hosts are the larval stage of the Angoumois grain moth, *Sitotroga cerealla*.

26. The apparatus of claim 25, wherein said quantity of selected insect hosts also includes a quantity of a preselected seed carrier for biologically supporting said moth larvae.

27. The apparatus of claim 25, wherein said exposure predetermined time period is approximately seventy-two hours for said moth larvae.

28. The apparatus of claim 18, wherein said insect hosts are the pupal stage of the Angoumois grain moth, *Sitotroga cerealla*.

29. The apparatus of claim 28, wherein said quantity of selected insect hosts also includes a quantity of a selected seed carrier for biologically supporting said moth pupae.

30. The apparatus of claim 28, wherein said exposure predetermined time period is approximately seventy-two hours for said moth pupae.

31. The apparatus of claim 18, further including shipping means for packaging said incubated parasitic mites and parasitized hosts for shipment to use as a biological control agent.

32. The apparatus of claim 31, wherein said shipping means comprises a shipping container for receiving said parasitic mites and parasitized hosts for commercial shipment, said container sealable to prevent escape of said parasitic mites but at least a portion thereof being constructed of a gas-permeable material that permits entry of air.

* * * * *